（12） United States Patent
Gustafsson et al.

(10) Patent No.: US 8,017,152 B2
(45) Date of Patent: Sep. 13, 2011

(54) CORES AND MICROCAPSULES SUITABLE FOR PARENTERAL ADMINISTRATION AS WELL AS PROCESS FOR THEIR MANUFACTURE

(75) Inventors: Nils Ove Gustafsson, Loddekopinge (SE); Monica Jonsson, Bara (SE); Timo Laakso, Malmo (SE)

(73) Assignee: Stratosphere Pharma AB, Malmo (SE)

( * ) Notice: Subject to any disclaimer, the term of this patent is extended or adjusted under 35 U.S.C. 154(b) by 1512 days.

(21) Appl. No.: 11/439,602

(22) Filed: May 24, 2006

(65) Prior Publication Data

US 2006/0269606 A1 Nov. 30, 2006

Related U.S. Application Data

(60) Provisional application No. 60/685,731, filed on May 27, 2005, provisional application No. 60/753,113, filed on Dec. 22, 2005.

(51) Int. Cl.
*A61K 9/14* (2006.01)
*A61K 9/46* (2006.01)

(52) U.S. Cl. ........ 424/489; 424/451; 424/452; 424/493; 424/496

(58) Field of Classification Search .......... 424/489–494, 424/451, 452, 496
See application file for complete search history.

(56) References Cited

U.S. PATENT DOCUMENTS

| | | | |
|---|---|---|---|
| 4,568,559 A | 2/1986 | Nuwayser et al. | |
| 4,623,588 A | 11/1986 | Nuwayser et al. | |
| 4,713,249 A | 12/1987 | Schroder | |
| 4,822,535 A | 4/1989 | Ekman et al. | |
| 5,405,616 A | 4/1995 | Wunderlich et al. | |
| 5,470,582 A | 11/1995 | Supersaxo et al. | |
| 5,578,709 A | 11/1996 | Woiszwillo | |
| 5,945,126 A * | 8/1999 | Thanoo et al. ............... | 424/489 |
| 5,981,719 A | 11/1999 | Woiszwillo et al. | |
| 6,120,787 A | 9/2000 | Gustafsson et al. | |
| 6,616,948 B2 | 9/2003 | Gustavsson et al. | |
| 6,753,014 B1 | 6/2004 | Sjoblom | |
| 2002/0044976 A1 | 4/2002 | Gustavsson et al. | |
| 2002/0045745 A1 | 4/2002 | Gustavsson et al. | |
| 2002/0081336 A1 | 6/2002 | Jonsson et al. | |
| 2002/0098203 A1 | 7/2002 | Gustavsson et al. | |
| 2002/0102311 A1 | 8/2002 | Gustavsson et al. | |
| 2003/0181371 A1 | 9/2003 | Hunter et al. | |

FOREIGN PATENT DOCUMENTS

| | | |
|---|---|---|
| EP | 0 145 240 | 6/1985 |
| EP | 0145240 | 6/1985 |
| EP | 0 576 675 | 1/1994 |
| EP | 0576675 | 1/1994 |
| WO | WO 97/14408 | 4/1997 |
| WO | WO 98/43664 | 10/1998 |
| WO | WO 99/03452 | 1/1999 |
| WO | WO 99/15154 | 4/1999 |
| WO | WO 01/19345 | 3/2001 |
| WO | WO 0119345 A1 * | 3/2001 |
| WO | WO 01/34646 A2 | 5/2001 |
| WO | WO 01/47560 | 7/2001 |
| WO | WO 02/28370 | 4/2002 |
| WO | WO 02/28375 | 4/2002 |
| WO | WO 02/28908 | 4/2002 |
| WO | WO 02/28909 | 4/2002 |
| WO | WO 03/080033 | 10/2003 |

OTHER PUBLICATIONS

Reslow et al., "Sustained release of human growth hormone (hGH) from PLG-coated starch microspheres", Drug Delivery Systems and Sciences, vol. 2, No. 1 (2003), 103-109.
Schwendeman et al. "New strategies of the microencapsulation of tetanus vaccine", J. Microencapsulation, vol. 15, No. 3 (1998), 299-318.
Artursson et al. "Characterization of Polyacryl Starch Microparticles as Carriers for Proteins and Drugs", J. Pharm. Sci., vol. 73 (1984), 1507-1513.
Laakso et al. "Biodegradable Microspheres IV. Factors Affecting the Distribution and Degradation of Polyacryl Starch Microparticles", J. Pharm. Sci., vol. 75 (1986), 962-967.
Laakso and Sjoholm "Biodegradable Microspheres X", J. Pharm. Sci., vol. 76 (1987), 935-939.
Stenekes et al. "The Preparation of Dextran Microspheres in All-Aqueous System", Pharmaceutical Research, vol. 15, No. 4 (1998), 557-561.
Franssen and Hennink "A Novel Preparation Method for Polymeric Microparticles without using Organic Solvents", Int. J. Pharm., vol. 168 (1998), 1-7.
Schroder "Crystallized Carbohydrate Spheres as a Slow Release Matrix for Biologically Active Substances", Biomaterials, vol. 5 (1984), 100-104.
Schroder "Crystallized Carbohydrate Spheres for Slow Release and Targeting", Methods Enzymol., vol. 112 (1985), 116-128.

\* cited by examiner

*Primary Examiner* — Michael G Hartley
*Assistant Examiner* — Micah-Paul Young (57) ABSTRACT

Process for producing parenterally administrable cores. The cores are intermediates suitable for manufacturing sustained release preparations. Microcapsules incorporating a core and a shell and pharmaceutical compositions incorporating such cores and microcapsules are also provided.

20 Claims, 2 Drawing Sheets

CORES AND MICROCAPSULES SUITABLE FOR PARENTERAL ADMINISTRATION AS WELL AS PROCESS FOR THEIR MANUFACTURE

This application claims the benefit of U.S. Provisional Application 60/685,731 filed on 27 May 2005 and U.S. Provisional Application 60/753,113 filed on 22 Dec. 2005. The entire content of such applications is hereby incorporated by reference as if fully set forth herein.

TECHNICAL FIELD

The present invention lies within the field of galenic formulations for the administration of biologically active substances (BASs hereinafter), more precisely microcapsules for controlled release intended for parenteral administration of said BASs. More specifically, the invention relates to production processes for such microcapsules containing said BASs and to the microcapsules thus obtained.

BACKGROUND OF THE INVENTION

There is a great need for controlled release formulations for BASs such as proteins, peptides and other drugs that are administered parenterally. Despite many published approaches, there is no entirely satisfactory technology.

Several features are desirable, alone or in combination, in such a technology. For example, it is desirable that the materials that are being used, often polymers, are approved by the regulatory authorities. In addition, it is desirable that the encapsulation of the BAS is done at high efficiency and retention of the integrity of the BAS, for example measured in terms of bioactivity. For BASs such as proteins that are dependent on their three-dimensional structure for retention of biological activity and for avoidance of, for example, undesired immune responses, it is desirable that the manufacturing process is able to retain the integrity of the substance. It is also desirable to control the release kinetics of the substance after administration, and in addition to the duration of the release, it is the variation of the release rate that is relevant. It is desirable to avoid too high a release initially after administration, which may lead to adverse effects and wasting of the BAS. Another feature that can be desirable, alone or in combination with one or more of those listed above or other features, is that the technology provide adequate release of the drug both when the content of drug in the formulation is low and high.

Injectable microcapsules comprising a core of highly branched, high molecular weight amylopectin and hGH and further comprising a release-controlling shell of a drug-free polymer are known (Reslow et al., Sustained release of human growth hormone (hGH) from PLG-coated starch microspheres. Drug Delivery Systems and Sciences, 2002, 2, 1 103-109).

A known technology for manufacturing of such coated microcapsules employs highly branched starch in an aqueous two-phase system (emulsion) where the solidification of droplets to microcapsules is obtained through the natural ability of the starch to gel (WO 97/14408, WO 02/28370), followed by coating using air suspension technology. This makes it possible to avoid exposing the BAS to an organic solvent. The long process time, however, is a disadvantage. Moreover, only one polymer, i.e. high molecular weight highly branched starch, is believed to have been demonstrated to work with this technology. In WO 02/28908, WO 02/28909 and WO 02/28370, highly specific requirements are described for this starch in order to manufacture parenterally administrable microcapsules and it is stated that the concentration of starch should be at least 20% for the manufacture of starch microparticles having good properties. Yet, the specific starch is not approved for parenteral administration by the regulatory authorities, and it can only be manufactured by a complicated purification process. In some cases it is desirable to have a higher content of biologically active substance than has been, or can be, obtained with this technology.

According to WO 02/28370, it is necessary that the solidification occurs through the natural tendency or ability of starch to gel, and not through, for example, precipitation with organic solvents.

Although many advances in controlled-release formulations for biologically active substances, including those for parenteral administration, are known, improvements would be desirable.

SUMMARY

The present invention relates to a process for producing parenterally administrable cores, said cores being intermediates suitable for manufacturing sustained release preparations, and microcapsules comprising a core and a shell, as well as to the cores and microcapsules as such. The invention further provides for a pharmaceutical composition comprising the microcapsules of the invention.

The invention involves improved manufacturing processes, and improved products, which realize one or more of the following advantages, alone or in combination with other advantages or features, in connection with cores suitable for coating using air suspension technology:

possibility of manufacturing cores containing a BAS which are suitable for coating by air suspension technology and useful intermediates in the manufacture of controlled release formulations,
  possibility of using polymers that are already approved for parenteral use as a matrix for the core,
  possibility of using several different polymers for manufacture the cores, separately or in combination,
  possibility of using different solidification principles in combination,
  possibility of manufacturing cores and microcapsules faster than with previously available processes,
  possibility of avoiding direct contact between the BAS and certain substances, for example a buffer substance, in the polymer matrix,
  possibility of encapsulating low molecular weight water-soluble substances efficiently, for example drugs and protein stabilisers, with high yield
  possibility to vary the content of BAS and any stabilisers within wide limits in the intermediates and microcapsules,
  possibility to obtain a higher content of BAS than previously possible with such cores and microcapsules,
  possibility to obtain high drug content with good control of the release properties, especially the burst release,
  possibility to apply more of at least one release regulating polymer to obtain desired release characteristics while still retaining a sufficiently high drug content in the obtained microcapsules.

The present invention discloses:
(1) A process comprising the following steps:
(a) preparing a polymer solution comprising at least one parenterally administrable polymer;
(b) providing a biologically active substance;

(c) combining the polymer solution of step a) with the biologically active substance of step b); and (d) dispersing the composition obtained in step c) as a discontinuous phase in a continuos phase.

(2) The process of (1) for preparing parenterally acceptable cores comprising a step e) of solidifying the composition obtained in step (d) to provide cores suitable for air suspension coating and having a size such that 80% of the material is in the range of 10-200 µm, in one embodiment 20-180 µm, said solidification optionally effected in the absence of a polymer dissolved in an organic solvent, especially a release controlling polymer, for example any of the shell polymers of the invention.

(3) The process of (1) or (2) where the BAS/core polymer ratio in step (c) is 0.1-99%.

(4) The process of (1) or (2) where the BAS/core polymer ratio is 30-99%.

(5) The process of (1) or (2) where the BAS/core polymer ratio is 40-99%.

(6) The process of (1) or (2) where the BAS/core polymer ratio is 50-99%.

(7) The process of (1) or (2) where the BAS/core polymer ratio is 60-99%.

(8) The process of (1) or (2) where the BAS/core polymer ratio is 70-99%.

(9) The process of any one of (1)-(8) where the polymer in step (a) is dissolved in an aqueous solution, optionally with addition of an organic solvent in a concentration not precipitating said polymer, for example in the range 1-40% (V/V), before or after said dissolution.

(10) The process of any one of (1)-(3) where the polymer concentration is in the range 20-65%, preferably 30-65.

(11) The process of any one of (1)-(3) and (10) where the BAS in step (b) is provided in dissolved or particulate form.

(12) The process of any one of (1)-(8), wherein the BAS in step (b) is provided in undissolved form, preferably as particles with a diameter less than 20 µm in diameter, more preferably less than 10 µm, optionally in the presence of at least one dissolution preventing substance as defined below.

(13) The process of any one of (1)-(9) in combination with (12) where the polymer concentration in step (a) is in the range 0.5-15%, preferably 0.5-10%.

(14) The process of any one of (2)-(13) wherein the solidification of step e) is carried out in the absence of chemical cross-linkers and/or substances that can polymerise by radical polymerisation.

(15) The process of any one of (2)-(14) wherein the solidification of step e) is carried out by exposure of the discontinuous phase to one or more organic solvents, formation of physical cross-links, generation of a complex, complex coacervation, freezing or a combination thereof.

(16) The process of any one of (1)-(15) wherein the continuous phase comprises one or more organic solvents, one or more oils, an aqueous solution containing one or more polymers, or a gas.

(17) The process of any one of (1)-(16) where the polymer in step a) is selected from the group of water soluble core polymers as defined below.

(18) The process of any one of (1)-(17) wherein the polymer is selected from any of the specific water soluble core polymers as defined below.

(19) The process of any one of (2)-(18), where the solidification of step e) is carried out within 16 hours, preferably within 8 hours, more preferably within 4 hours, and most preferably within 2 hours.

(20) The process of any one of (1)-(19) wherein the polymer of step a) has a low content of low molecular weight substances, as defined below.

(21) The process of any one of (1)-(20) wherein the BAS is selected from protein drugs and low molecular weight drugs, optionally from the specific subclasses of protein drugs as defined below.

(22) The process of any one of (1)-(21), wherein the BAS is selected from the specific protein BASs as defined below.

(23) The process of any one of (2)-(22), wherein the solidified cores are dried by lyophilisation, vacuum or by fluidising in an air suspension apparatus.

(24) The process of any one of (2)-(23) comprising applying one or several core surface substances onto the cores, by spraying in an air suspension coating machine, said substances preferably being selected from those that can stabilise pH, prevent or reduce aggregation, improve stability or influence the release kinetics of the BAS.

(25) The process of (24) where the core surface substance is dispersed in a polymer or, preferably, in the absence of a polymer.

(26) The process of (24) or (25) wherein the amount of core surface substance is in the range of 0.1-30%, or 0.2-25%, or 0.4 to 20% or even 0.8-15%.

(27) The process of any one of (24)-(26) wherein the core surface substance is particulate and has a diameter below 10 µm, or less than 5 µm, or less than 2 µm, or even less than 1 µm.

(28) The process of any one of (24)-(27) where the substance is a buffer substance.

(29) The process of (28) where the buffer substance is selected from the specific core surface substances as defined below.

(30) A process of preparing a parenteral sustained release microcapsule, comprising the application of a release controlling shell onto the core obtainable according to any one of (2)-(29).

(31) The process according to (30) wherein the shell comprises one or more film-forming, biodegradable and parenterally administrable polymers or copolymers.

(32) The process according to (30) or (31) wherein the polymer or copolymer is selected from the specific shell polymers as defined below.

(33) The process of any one of (30)-(32) wherein the polymer or copolymer comprises alpha-hydroxy acid repeating units.

(34) The process of (33) wherein the alpha-hydroxy acid is lactic acid and/or glycolic acid.

(35) The process of any one of (30)-(34) wherein the process for applying the release controlling shell is selected from air suspension coating, spray drying, or an emulsion based process, optionally comprising in-water-drying, with air suspension coating being preferred.

(36) The process of any one of (30)-(35) wherein the release controlling polymer is applied by air suspension coating and the ratio of polymer applied is about 0.3 to 10, or 0.4 to 6, or 0.5 to 2, or about 0.6 to 1.1 gram per gram of cores.

(37) The process of any one of (30)-(36) wherein the composition and the amount of the release controlling polymer is selected so that the duration of release of the BAS is in the range of 3 days to about one month, optionally in the absence of any lag-phase and without any explosion of the coating.

(38) The process of any one of (30)-(37) wherein at least one aggregation preventing substance as defined below is added onto the surface of the microcapsules.

(39) The process of (38) where the substance is selected from the specific groups of aggregation preventing substances as defined below.

(40) The process of any one of (1)-(39) wherein the core polymer is not Amioca 50 or amylopectin with an molecular weight where 80% is above 10 kDa, optionally when the polymer concentration is higher than 10%, preferably higher than 20.
(41) The process of any one of (1)-(8) where the polymer in step (a) is dissolved in at least one organic solvent, said polymer being selected from water insoluble or very slightly water-soluble synthetic or semi-synthetic polymers.
(42) The process of (41) wherein the polymer is selected from the water-insoluble core polymers as defined below.
(43) The process of (41) or (42) in combination with any one of (21)-(23).
(44) The process of any one of (41)-(43) in combination with any one of (30)-(39).
(45) A parenterally acceptable core, said core comprising: (a) at least one parenterally administrable water soluble polymer, and (b) at least one parenterally administrable biologically active substance, wherein the content of said biologically active substance is at least 30 percent by dry weight of the combined weight of said water soluble polymer and said biologically active substance.
(46) The core of (45) wherein 80% of the intermediate is in the range of 10-200 µm, preferably 20-180 µm, in diameter.
(47) The core of (45) or (46), wherein the content of said BAS is at least 40 percent, preferably at least 50 percent, more preferably at least 60 percent, and most preferably at least 80 percent.
(48) The core of any one of (45)-(47) that releases at least 80%, preferably at least 95%, and most preferably essentially 100% of the encapsulated BAS within 3 days, preferably 1 day, in vitro or in vivo.
(49) The core of any one of (45)-(48) wherein the parenterally administrable polymer is selected from the group of water soluble core polymers as defined below, preferably consisting of one polymer.
(50) The core of any one of (45)-(49) wherein said polymer is selected from any of the specific water soluble core polymers as defined below.
(51) The core of any one of (45)-(50) wherein the BAS is selected from protein drugs and low molecular weight drugs, optionally from the specific subclasses of protein drugs as defined below.
(52) The core of (51) wherein the BAS is selected from the specific protein BASs as defined below.
(53) The core of (52) wherein the BAS is present as discrete particles in the core.
(54) A sustained release microcapsule comprising a core according to any one of (45)-(53) and a release-controlling shell of one or more film-forming polymers or copolymers.
(55) The microcapsules of (54), which have a content of biologically active substance of at least 15 percent by dry weight.
(56) The microcapsules of (55) which have a content of biologically active substance of a least 20 percent, preferably at least 30%, by dry weight.
(57) The microcapsules according to any one of (54)-(56), wherein the shell polymer or copolymer comprises alpha-hydroxy acid repeating units, said units preferably being lactic acid and/or glycolic acid.
(58) The microcapsules according to any one of (53)-(57), comprising at least one functional substance as defined in any one of (24)-(29), or any combination thereof, characterised in that the biologically active substance and said functional substance are essentially not in direct contact with each other.
(59) The microcapsules according to (58), wherein the functional substance is a solid buffer substance essentially localised between the biologically active substance and the release-controlling shell, and is preferably not dispersed in a polymer.
(60) The microcapsules according to any one of (57)-(59) that remain a free flowing powder when exposed to a temperature corresponding to and up to 15° C. above the glass transition temperature of the release regulating polymer or polymers, which preferably are arranged so that they form a coating or shell.
(61) Microcapsules according to any one of (53)-(60) wherein the core and the shell can be distinguished from each other by electron microscopy.
(62) Microcapsules according to any one of (54)-(61) wherein at least 50%, or at least 80%, or at least 90% or even at least 98% of the microcapsules have one single distinct core.
(63) Microcapsules according to (62) where said single core has a diameter which is at least half, preferably ¾, the diameter of the diameter of the entire microcapsule.
(64) Microcapsules according to any one of (53)-(63) which can be injected through a 21 G needle or finer, preferably a 23 G needle or finer, most preferably 25 G needle or finer.
(65) Microcapsules according to any one of (53)-(64) wherein the integrity of the BAS is essentially retained.
(66) Microcapsules according to any one of (53)-(65) characterised in that the release during the first 24 hours after administration is less than 20%, preferably less than 10%.
(67) The subject-matter according to any one of (1)-(66) where the BAS is not a substance administered with the intention or potential of raising an immune response, for example antigens, vaccines or viruses, and the composition does not contain any other component that is known to be able to induce an immune response.
(68) The subject-matter according to any one of (1)-(66) wherein the BAS comprises a substance that is administered with the intention or potential of raising an immune response, for example antigens, vaccines or viruses; optionally wherein said compound is released in either two distinct phases, defined herein as pulsed release, or in one phase delayed with at least 1 month, preferably at least 3 months after administration.

DETAILED DESCRIPTION OF PREFERRED EMBODIMENTS

Polymers useable in the present invention, particularly in forming the core or in forming the shell, are all biocompatible polymers, without limitation, i.e. they are, or can become, approved for parenteral administration. If used for forming a core, they can be dissolved in water or an aqueous medium, or in mixtures of organic solvent and water, and can be solidified to discrete solid units, i.e. cores, which contain a BAS using any of the solidification principles disclosed in this invention, and which can be coated by air suspension technology. These polymers will be referred as water soluble core polymers in this invention. In another embodiment they can be dissolved in an organic solvent or mixtures of organic solvents and will be referred to as water insoluble core polymers in this invention. If used for forming a shell, they can be dissolved in an organic solvent and can be applied onto the cores to form the shell and are referred to as shell polymers, or coating polymers.

The polymers are preferably biodegradable. The polymers are preferably chosen from those that are already being used in parenteral formulations for mammals such as humans.

In this invention, all percentages are by weight, unless stated otherwise. In this invention, the content of BAS is expressed as weight percentage and is calculated as the dry weight of the BAS divided by the combined dry weight of the BAS and the polymer (in the following referred to as BAS/core polymer ratio) in the core. The content of BAS in the microcapsules is expressed as the dry weight of the BAS divided by the dry weight of the microcapsules. In this invention, "diluent particles" is defined as particles with a size below 20 μm in diameter, preferably below 10 μm in diameter, which do not contain any BAS. Said diluents can be selected from particles comprising at least one substance of the following group: monosaccharides, disaccharides, oligosaccharides, polysaccharides, polyamino acid, glycosaminoglycan (mucopolysaccharide), water-soluble synthetic polymers, solid buffer substances and water-insoluble polymers. Said water-insoluble polymers of the diluent particles include all the polymers suitable for forming the core or the release controlling shell.

In this invention, the molecular weight of substances having a molecular weight distribution is defined functionally as the ability to pass a membrane with a certain pore size corresponding to a certain molecular weight, as indicated by the manufacturer. In particular, the molecular weight of a substance can be characterised by its molecular weight cut off (MWCO) value. The content of low molecular substances in those polymers that are being used to manufacture the cores can thus easily be determined by anyone skilled in the art by exhaustive dialysis and determination of the amount that has passed through said membrane.

For example, the fraction having a molecular weight below 3.5 kDa or 10 kDa is determined using dialysis, preferably with regenerated cellulose membranes, with an MWCO of approximately 3.5 kDa and 10 kDa, respectively. Most preferably, Spectra/Por® 3 and 7 (Spectrum Laboratories, Inc., Rancho Dominguez, Calif.) are used. The dialysis is carried out under conditions that maintain the substances in dissolved state, for example at a sufficiently high temperature, preferably approximately 55° C., using purified or distilled water as the dialysate, a ratio between dialysate and sample volume of at least 100, a duration of 3 days and changing the dialysate twice each day. The amount of the substance in the combined dialysate is determined, if necessary after drying and re-dissolution in a smaller volume, by methods known in the art, for example dry weight determination, amino acid analysis or enzymatic degradation followed by glucose determination.

In this invention, the term "low content of low molecular weight substances" in connection with a polymer, in one embodiment a water soluble polymer, means that the content of the polymer fraction having a molecular weight of less than 3.5 kDa is less than 5%, in one embodiment less than 3%, in one embodiment less than 1% and in one embodiment less than 0.5%. The reduction of the content of low molecular weight substances can be achieved by methods known in the art, for example dialysis, trans-flow or cross-flow filtration.

In this invention, the term "low amino acid nitrogen content" or "low protein content" means that the content, expressed as μg amino acid nitrogen per gram dry weight of polymer, is less than 20, in one embodiment less than 5, in one embodiment less than 1 or even lower. The amount of protein in a polysaccharide can be determined by methods known in the art. One method in accordance with the invention is the determination of amino acid nitrogen content by amino acid analysis.

In this invention, "core surface substances" is defined as substances that are applied onto the cores prior to application of a release regulating shell. Said substances can be selected from those that can stabilise pH, prevent or reduce aggregation, or improve or control the release kinetics or stability of the BAS. Buffer substances are used in one set of embodiments. It has been found that it is possible to apply those substances that have a reduced solubility in water, for example zinc oxide, in the form of solid particles without the use of a binder, and this defines one set of embodiments of the invention. The amount of functional substance can be in the range of 0.1-30%, or 0.2-25%, or 0.4 to 20% or even 0.8-15%. The particle size of the functional substance can be below 10 μm, or less than 5 μm, or less than 2 μm, or even less than 1 μm. The substance may be a buffer substance. Examples of suitable particulate substances include magnesium carbonate, magnesium hydroxide, magnesium oxide, magnesium trisilicate, zinc carbonate, zinc hydroxide, zinc oxide, aluminium hydroxide, calcium carbonate, basic aluminium carbonate, ammonium phosphate, calcium phosphate, calcium hydroxide and magaldrate. Zinc carbonate and zinc oxide are preferred. Zinc oxide is used in one set of embodiments.

In this invention, "core polymers" are those dissolved in step a) of the process. In one aspect of the invention, said polymers are water soluble and referred to herein as "water soluble core polymers". In one set of embodiments, said polymers can be chosen from the following groups: polyamino acids, polysaccharides, glycosaminoglycans (mucopolysaccharides) and water-soluble synthetic polymers.

In one aspect of the invention, said polymer is not soluble in water, and referred to herein as a "water insoluble core polymer". In one set of embodiments, said polymers are chosen from the following groups: water insoluble or very slightly water-soluble synthetic or semi-synthetic polymers. Terms of solubility, such as "soluble", "slightly soluble", "very slightly soluble", etc., are defined in accordance with the Handbook of Pharmaceutical Excipients (Third edition, edited by Arthur H. Kibbe, 2000, American Pharmaceutical Association and Pharmaceutical Press).

The "specific water soluble core polymers" of the invention include the following: (1) polyamino acids including collagen, atelocollagen, protamin, polyarginine and polyornithine; (2) polysaccharides including amylopectin, sodium carboxymethylcellulose, maltodextrin, dextran and glycogen; (3) glycosaminoglycans (mucopolysaccharides) including hyaluronic acid, chondroitin sulphate and dermatan sulphate; (4) water soluble synthetic polymers including polyvinylpyrrolidone (PVP) and polyethyleneglycol or polyethyleneoxide (both referred to as PEG from hereon). Preferably, as there is a risk that gelatin derived from animal sources may generate an immune response, such gelatin is not used in one embodiment of the invention. However, in another embodiment, gelatin of non-animal source, such as recombinant gelatin, may be used as the water-soluble core polymer.

The specific "water-insoluble core polymers" include polytartrate, polyanhydrides, polyorthoesters, benzyl esters of hyaluronic acid, polyacetals, poly(ethylene carbonate)

copolymers, and copolymers comprising hydroxyl groups and the above-mentioned polymers based on lactic or glycolic acid, for example glucose-PLGA. Mixtures of polymers can be used. Said polymers are well known to the person skilled in the art.

Hyaluronic acid is a naturally occurring glycosaminoglycan (mucopolysaccharide) consisting of a linear polymer with repeating units of glucuronic acid and N-acetylglucosamine. Sodium hyaluronate is included in the Pharmacopoeia and is used for ocular, intraarticular and parenteral administration either in chemically un-modified or modified form. In the present invention, hyaluronic acid is defined to comprise all parenterally administrable forms, for example, hyaluronic acid; salts, such as sodium hyaluronate, calcium hyaluronate, zinc hyaluronate; complexes, such as those with benzalkonium chloride and BASS; ionically cross-linked forms, such as those with $Fe^{3+}$; chemically modified forms, such as esters, for example benzyl esters; and forms which have been chemically cross-linked prior to being used in step a) of the process of the present invention. The same applies to other parenterally administrable glucosaminoglycans (mucopolysaccharides), for example chondroitin sulphate and dermatan sulphate. The molecular weight for hyaluronic acid is not limited, but can be in the range 50-5000 kDa or 400-4000 kDa.

Collagens, or polymers obtained thereof like atelocollagen and gelatin, can be selected from those that are being used in products approved for parenteral administration, preferably those that are manufactured by recombinant means. Atelocollagen is selected in one embodiment. Gelatin useful in this invention is preferably recombinant gelatin and is not derived from an animal source. In one set of embodiments, the polymers have a low content of low molecular weight substances.

The molecular weight for amylopectin usable in the present invention is, in one embodiment, in the range of 3-3000 kDa, in one embodiment 3-900 kDa. The molecular weight for amylopectin in one embodiment is characterised in that at least 60% by weight, or 80% by weight, or even 90% by weight or 100% by weight thereof is below 10 kDa. In one set of embodiments, the amylopectin has a low content of low molecular weight substances, which provides improved properties, especially in relation to solidification properties, for example the rate of solidification.

In one aspect, the present invention is directed to parenterally administrable maltodextrin defined in this invention as having an average molecular weight below 10 kDa and a low amino acid nitrogen content. In one embodiment, the maltodextrin has a low content of low molecular weight substances. It has surprisingly good properties for the preparation of microspheres containing BASs, both in dissolved or particulate form. It can be manufactured from commercially available maltodextrin by reduction of protein content and the content of low molecular weight substances, both of which can be accomplished by methods known in the art.

Additional details for PLGA, sodium carboxymethyl cellulose, gelatin, maltodextrin, PEG and PVP can be found in the Handbook of Pharmaceutical Excipients (supra).

In accordance with one aspect of the invention, the content of proteins in the polysaccharides or glycosaminoglycans, for example maltodextrin, amylopectin, sodium carboxymethyl cellulose, glycogen or hyaluronic acid, is reduced. This may be necessary to obtain a sufficiently high purity for parenteral administration, especially for repeated parenteral administration. In one embodiment, the reduction is carried out by ion exchange chromatography, for example anion exchange chromatography, which has been described in detail in WO 02/28908 and WO 02/28909. In addition, the content of low molecular weight substances is reduced with methods known in the art. Additional steps, such as filtration to remove undissolved material or precipitates, and removal of endotoxins by methods known in the art, may be used. Said reduction of low molecular weight substances, undissolved material or precipitates, and endotoxins, can be applied to any of the water soluble core polymers of this invention.

In one embodiment, only one polymer is used for the manufacture of the cores. In one embodiment said core polymer is selected so that it biodegrades to chemically neutral species and not acidic degradation products. In another embodiment, only one polymer selected from the water soluble core polymers of the invention is used. Maltodextrin is preferred when the core loading with BAS is in the range of 0.1-20%, and hyaluronic acid is preferred when the content of BAS in the core is in the range of 30-99%, or hyaluronic acid is preferred when the content of BAS in the core is in the range of 0.5-80% and when diluent particles are used.

The polymers are dissolved in a solvent according to methods known in the art, for example by heating. The concentration of the polymer, or polymers, is without limitation as long as the cores obtained have the desired content of BAS and a size distribution and mechanical integrity acceptable for air suspension coating.

Protein stabilisers, buffer substances, surface active substances, substances used to adjust the solubility of the BAS and/or core polymer and substances used to adjust the osmolarity of the solution can be added. When concentrations exceeding 1% and/or a prolonged effect are desired, said substances are preferably used in solid form. Examples include sucrose, gelatin, trehalose, mannitol and solid buffer substances.

In one embodiment, the BAS is in a dissolved form when mixed with the polymer in step c).

In one embodiment, the BAS is in an undissolved form when mixed with the polymer in c), preferably as particles with a diameter of less than 20 μm, preferably less than 10 μm, for example in a form that allows retaining its integrity in the process and achieving an acceptable yield. For the purpose of this invention, the term undissolved form in connection with the BAS means that the BAS in practice can be handled as small particles prior to shaping the composition of the present invention in step e) of the process. The BAS may be present in any form, for example: amorphous, semi-crystalline or crystalline; it may be complexed to parenterally administrable complexing agents and stabilizers; it may constitute a precipitate obtained using any parenterally administrable complexing agent or mixtures of complexing agents; or have been precipitated or highly concentrated using polymers, for example polyethylene glycol, amylopectin, maltodextrin, hyaluronic acid; it may be have been converted into solid form by heating or cooling, for example freezing, optionally in the presence of polymers, e.g. PEG; it may be formed into small particles by using a supercritical fluid as the external phase fluid and rapid pressure release, it may be encapsulated in nanoparticles, microparticles, liposomes or solid lipid dispersions in particulate or dissolved form; it may be encapsulated in or constituting a dispersed phase which is not miscible with the solvent used to dissolve the core polymer, for example droplets not miscible with water.

In one embodiment, the BAS is converted to particulate form by immobilisation or encapsulation in particles comprising or consisting of at least one low molecular weight substance, referred to herein as "low molecular weight core substances", either prior to forming the cores or in connection with the formation of the cores. Said low molecular weight substances can be selected, without limitation, from any that can be administered parenterally and can provide said immobilisation of the BAS, with water soluble substances being preferred. Groups from which the low molecular weight substance can be selected include monosaccharides, disaccharides, oligosaccharides and amino acids. In one embodiment, the low molecular weight substance is sucrose or trehalose.

When used in undissolved form the BAS is suspended in a medium such as water, an aqueous solution or an organic solvent, with or without additional substances. When said substances are selected with the purpose to maintain the BAS in undissolved or essentially undissolved form, they are referred to herein as "dissolution preventing substances". Said substances are selected from those that can be administered parenterally. Examples are low molecular weight, such as those having a molecular weight of less than 50 kDa, or less than 1000 Da, and macromolecular complexing agents, pH adjusting agents, water miscible organic solvents and water soluble polymers. Specific examples include divalent ions like zinc and calcium, PEG, gelatin, amylopectin, maltodextrin, phosphate, citrate, hydrogencarbonate and the like.

To provide dilution to a desired concentration of BAS and/or polymer in the core, and/or to provide stabilisation of said BAS, diluents or diluent particles may be added to the suspension of BAS or the solution of core forming polymer, or both.

The mixing of the BAS and the core polymers (step (c)) can be carried out by conventional methods. The BAS may be added to the polymer solution, or vice versa. The temperature is selected based on the solubility properties of the polymer solution and the temperature sensitivity of the BAS. The temperature is below 60° C. in one set of embodiments, optionally below 50° C. Lower temperatures may be preferable to support retaining integrity of the BAS.

The BAS is selected from those that can be administered parenterally to elicit a beneficial or therapeutic effect. In one preferred embodiment, substances are excluded that are administered with the intention or potential of raising an immune response, for example antigens, vaccines or viruses, said excluded substances being defined herein as immunologically active substances (abbreviated as IAS).

The BAS may be selected from protein drugs, or non-protein drugs. Protein drugs, which include peptides, can be selected from the following specific subclasses: glycosylated proteins, non-glycosylated proteins, recombinant proteins, chemically modified proteins, growth factors, cytokines, blood coagulation factors, peptides, T-cell immunity regulating enzymes, peptide analogues, somatostatin analogues, monoclonal antibodies and modified monoclonal antibodies.

Specific examples of protein BASs in this invention are human growth hormone, erythropoietin, interferon (for example type alpha, beta or gamma), Factor VII, Factor VIII, LHRH-analogues, glucagon-like peptides (GLP), insulin like growth factor I, C-peptide, bone morphogenetic protein, octreotide follicle stimulating hormone, epidermal growth factor, insulin, macrophage colony stimulating factor, macrophage granulocyte stimulating factor, indoleamine 2,3-dioxygenase, granulocyte colony stimulating factor, triptorelin, and interleukin. Particularly preferred protein BASs for use in the present invention are human growth hormone, erythropoietin, interferon gamma and glucagon-like peptides. Analogues or fragments of the above substances and macromolecules with similar therapeutic function are also included in the invention.

In one embodiment, the non-protein BASs may be selected from those with a low molecular weight, defined in this invention as generally below 3.5 kDa, preferably below 1 kDa. In one embodiment, said non-protein BASs may be selected from antitumour agents, antibiotics, anti-inflammatory agents, antihistamines, anti-alcohol dependence substances, sedatives, muscle-relaxants, antiepileptic agents, antidepressants, antiallergic agents, bronchodilators, cardiotonic agents, antiarrhythmic agents, vasodilators, antidiabetics, anticoagulants, haemostatic agents, narcotics and steroids. Specific examples include risperidone, naltrexone, morphine, bupivacaine, loperamide and indoleamine 2,3-dioxygenase inhibitors. In one embodiment, the BAS is low molecular weight heparine.

The composition in step e) is shaped, preferably so that particles suitable for coating using air suspension technology, for example in terms of size distribution, can be obtained. Said shaping is carried out in the absence of any compounds that cannot be administered parenterally and cannot be removed in subsequent process steps. In one embodiment of manufacturing the core, an aqueous discontinuous phase containing the core polymer and the BAS is created in a continuous phase to shape the composition obtained in step c). The size of the discontinuous phase, for example the droplets, is preferably selected so that the cores obtained have a size such that 80% of the material is in the range of 10-200 μm, preferably 20-180 μm in dry state. The continuous phase can comprise an organic solvent or oil, an aqueous polymer solution or a gas. For using a gas as the continuous phase, reference is made to U.S. Pat. No. 6,753,014, the disclosure of which is incorporated in its entirety. In one embodiment, the continuous phase comprises an oil.

In one embodiment, the continuous phase constitutes an organic solvent or an oil, which are immiscible or essentially immiscible with water. The continuous phase can be a mixture of two or more organic solvents or oils, or a combination thereof. Said organic solvents and oils are well known to the person skilled in the art and include ethyl acetate, ethyl oleate, benzyl benzoate, isopropyl myristate, methylene chloride, chloroform, medium chain triglycerides, paraffin oil, silicone oil and vegetable oils such as coconut oil, sesame oil, arachis oil, castor oil, cottonseed oil, rape seed oil and corn oil.

In another embodiment, the continuous phase is an aqueous solution which contains at least one polymer or other substance which enables the creation of an aqueous two-phase system in combination with the discontinuous phase of the core polymer and the BAS. Polymers and other substances having the ability to form an aqueous two-phase system are known in this art. The most preferred polymer is polyethylene glycol. Molecular weights can be 5-35 kDa, or 15-25 kDa, or about 20 kDa. The polymer is dissolved in a suitable concentration in water or in aqueous solution, which may contain for example buffer substances and salts. The concentration can be 20-55% by weight, or 25-45% by weight, or 30-40% by weight.

The temperature of the continuous phase can be in the range of from −196° C. to 60° C. For gases it can be an advantage to select the temperature to be below the freezing point of the discontinuous phase, for example by at least 20° C. Before the continuous phase is mixed with the aqueous solution of the core polymer and the BAS, the temperature of the former may then be adjusted to a temperature that is not harmful for the BAS, for example 50° C. or lower.

In one set of embodiments, the discontinuous phase and the continuous phase form a W/O emulsion. Surface active agents known to the person skilled in the art can be used to stabilise the emulsion. This embodiment provides good control of the concentration of, for example, the polymer in the discontinuous phase, since the rate of the water transport to the external phase can be made very low. It can also provide a high yield of substances that would have diffused out into an aqueous continuous phase.

After a suitable time, the droplets forming the discontinuous phase are solidified to discrete units (step (e)). In this invention, "solidification" means that the discontinuous phase, finely dispersed or existing as small droplets, is converted into solid form (cores) with a size distribution that allows coating with air suspension technology. Said solidification is preferably effected in the absence of a polymer dissolved in an organic solvent, especially a release controlling polymer, for example any of the shell polymers of the invention, since it is desired that the release controlling shell, applied in subsequent steps, is to control the release.

Solidification can be carried out in several ways. Fundamental for the choice of the solidification principle is that the integrity of the BAS is retained at an acceptable level. This means that the core polymer is preferably solidified without covalent modification or chemical cross-linking and in the absence of radically polymerizable substances. The core polymer may have been modified covalently or chemically cross-linked prior to being mixed with the BAS or used in the process of this invention. It further means that the solidification is preferably carried out in the absence of substances that can denature proteins, at least at harmful concentrations for the particular form of active substance that is used, and in the absence of polymers and other substances that cannot be administered parenterally. It further means that the solidification is preferably carried out by avoiding heating to temperatures that are detrimental for the BAS, for example above 60° C.

In this invention, solidification further means that the cores are optionally converted to the dry state. Drying is usually necessary to obtain the dried cores, preferably in free-flowing or similar form, with sufficient mechanical stability to withstand coating using air suspension technology.

A first solidification principle or method useful in accordance with the invention is to remove or reduce the water content in the discontinuous phase containing the core polymer and the BAS by exposing it to a suitable organic solvent miscible with water. Mixtures of different organic solvents can be used and also mixtures of these with water. Removing or reducing the water content or dehydration refers to the removal of water to such an extent that solid cores are obtained. In this step, an entirely dry preparation is not necessarily obtained. The organic solvents are chosen from those that are acceptable for the manufacture of parenteral formulations, can accomplish sufficient dehydration to provide solid units that can be worked up and subsequently dried, and provide acceptable retention of the integrity of the BAS. Examples include acetone, ethanol, methanol, isopropanol and ethyl acetate. It has been found possible to retain the integrity of even some sensitive recombinant proteins despite exposure to properly selected organic solvents. It is preferred to use an excess of organic solvent to effect the solidification rapidly. Generally, it is useful in one embodiment to use at least 3-100 times the volume of organic solvent compared to the volume of water in the discontinuous phase.

A second, alternative solidification principle is the formation of physical cross-links, or utilisation of the capability of a polymer to solidify. This solidification principle is generally chosen when the BAS does not retain its integrity sufficiently when the solidification is carried out through exposition to an organic solvent, since for example the work up and drying processes tend to become more time-consuming and complicated. When correct conditions have been chosen, such as core polymer, time allowed for solidification and temperature, it is possible to solidify for example gelatin, atelocollagen, maltodextrin and amylopectin, especially when these have a low content of low molecular weight compounds, using this principle.

It has been found that the maltodextrin having a low content of low molecular weight substances can be solidified according to this principle within a short period of time. In the embodiment where solidification is achieved solely by formation of physical cross-links, e.g., by the natural capacity of the polymer to gel, especially within a time period of not longer than 16 hours, or not longer than 8 hours or 4 hours, the discontinuous phase does not, in one set of embodiments, comprise: a solution of starch that is not parenterally administrable or a solution of a highly branched starch where 80% of the material is within the molecular weight range 10-10 000 kDa, 40-800 kDa or 200-600 kDa in combination with an amino acid nitrogen content higher than 50, or 20, or 10 or 5 µg amino acid nitrogen per gram. For example, use of non parenterally administrable amylopectin, for example starch by the trade name of Amioca 50 (National Starch), or any starch with the same or similar properties, may be avoided.

A third solidification principle that can be used in the invention comprises the formation of a complex having reduced solubility and being able to form a precipitate. Said complex can be formed between the core polymer and another polymer, between the core polymer and a BAS, or between the core polymer and a low molecular weight substance. Examples include gelatin-hyaluronic acid, hyaluronic acid—benzalkonium chloride and the like.

A fourth solidification principle that can also be used is freezing of the discontinuous phase followed by lyophilization, for example in a spray or in an emulsion. It has been found that cores having BAS/core polymer ratios as defined in (2)-(8) above and comprising only materials acceptable for manufacturing parenteral preparations and for air suspension coating, can be obtained by rapid freezing of droplets containing at least one BAS, preferably in solid form, and at least one core polymer, using a cold or liquefied gas, for example liquid nitrogen, using a concentration of the core polymer of lower than 5% based on dry weight. The skilled person will appreciate that solidification may occur in either one or both of the cold or liquefied gas. In this solidification principle, the core polymers act as a polymeric binder. In one embodiment, the core polymer is selected from the specific water soluble core polymers of this invention or the specific water insoluble core polymers of this invention, the BAS/core polymer ratio is as defined in any of (2)-(8) above and the concentration of the core polymer is less than 4%, preferably less than 3%. In one embodiment the BAS/core polymer ratio is as defined in any of (2)-(8) above, the core polymer is selected from the specific water soluble polymers of this invention and the concentration of core polymer, preferably sodium hyaluronate, is about 2.5% or lower. Diluent particles can be used as appropriate to obtain the desired BAS and/or dry content. In each case, the frozen water is removed after the solidification. Examples of methods include extraction with an organic solvent, for example acetone which is preferred when other substances, for example PEG, is also to be removed, or preferably by sublimation, which is preferred in all other cases.

A combination of the above described solidification principles can also be used in the invention. For example, physical cross-linking is allowed to occur over a period of time after which water is removed, for example by exposure to an organic solvent, enabling reductions in process times as compared to previously available technologies. Additionally, improved solidification can be achieved by changing the pH and/or ionic strength, particularly in the case of atelocollagen, or by adding a complex forming substance at the appropriate step in the process to obtain more rapid solidification or improved solid properties.

Another solidification principle that can be used in the invention comprises removal of organic solvent. This can be accomplished by means known in the art. In one embodiment the removal is effected by exposure to another organic solvent miscible with the first organic solvent and able to solidify the core polymer. In another embodiment, the removal is effected by exposure to an aqueous phase miscible with the organic solvent. In another embodiment, the removal is effected by in-water-drying, preferably by heating or reduced pressure, of an oil-in-water, or solid-oil-water, or water-oil-water emulsion. This solidification principle can be used when the BAS can be exposed to the organic solvent with retained integrity and the polymer, or polymers, used to form the core can be dissolved in the organic solvent.

For any of these solidification principles, or combinations of these, the solidification is allowed to continue as long as is required to obtain acceptably solid cores. For some combinations of polymers and the BASs, it can be a matter of 24 hours or longer. Generally, the solidification should be completed as soon as possible after creating the discontinuous aqueous phase of BAS and specific polymer in the continuous phase. In one embodiment, the solidification be completed within 16 hours from said mixing. In many cases, the solidification is effected within 8 hours, or within 4 hours or even within 2 hours.

The solid cores manufactured by the processes described above may be separated by methods known in the art. For example, sedimentation, filtering or washing by centrifugation can be used to remove the continuous phase and added organic solvent.

After the solidification and optional work up, including separation, the cores may be dried. Any drying method can be used. Preferably, the drying method is selected such that the integrity of the BAS is retained sufficiently, adequate drying is obtained and the integrity of the cores is retained. Examples of drying methods are air-drying, vacuum drying, freeze-drying and drying using a fluidised bed, or air suspension drying. The diameter of the cores is preferably determined after the drying step. In one embodiment the drying is carried out at a temperature below 60° C. In order to shorten the processing time, the drying can be carried out in the equipment subsequently used for the air suspension coating, or in equipment with comparable capability for drying of small particles.

In those cases where the cores display agglomeration, agglomeration can be kept below 10% by volume in one set of embodiments, or lower than 5% or even lower than 2%. Agglomeration can be kept low by means of the choice of the components in the cores, the solidification and drying methods, and/or by the use of agents that modify the surface of the cores during solidification (for example, complexing agents) or work up (for example mannitol in the acetone used for washing). A higher percentage of agglomeration may be acceptable where the air suspension coating results in de-agglomeration. When air suspension drying is used, the evaluation of the degree of agglomeration is made, for example, when the cores are ready for the application of a core surface substance or a release-controlling shell, or in one set of embodiments after the release-controlling polymer and optional aggregation preventing substance has been applied onto the cores.

The integrity of the BAS after encapsulation in the cores of the invention, can be determined with methods known in this art. When this determination is carried out in vivo, the cores or microcapsules are administered parenterally, possibly in dissolved form, and the effect is compared with the one obtained with the same amount of the BAS in a suitable form, for example in solution. When it is required that the biologically active substance is in dissolved form, for example in some in vitro assays, the substance can be allowed to diffuse out of the core in an aqueous medium or the cores can be dissolved. The preferred methods are changing the solvent, the pH, heating or enzymatic treatment, or combinations thereof. Gelatin and collagen can be dissolved using collagenase and gelatinase, for example matrix metalloproteinase 2. Cores made of amylopectin or maltodextrin can be dissolved using alpha-amylase and/or amyloglucosidase, optionally in combination, and cores of hyaluronic acid by hyaluronidase. Cores made of PLGA and other polymer soluble in organic solvents can be dissolved by exposure to organic solvent, by procedures known in the art, and if appropriate dried whereafter the BAS can be dissolved for analysis.

In one preferred embodiment, the process further comprises a step of applying a release controlling shell onto the cores, said cores being intermediates for preparing a sustained release formulation. Said application can be carried out by emulsion or spraying based processes. In the emulsion based processes, it is preferred to use the preformed cores, as defined above, in dry form. The cores are suspended in a solution of the release regulating polymer, or polymers, dissolved in at least one organic solvent. Water or buffer can be added in an amount sufficient to wet but not to dissolve the cores to, for example, improve precipitation of the release regulating polymer onto the cores. Deposition of said polymer onto the cores can be obtained by interfacial precipitation, addition of anti-solvent, or removal or organic solvent by extraction or evaporation, optionally after freezing, or the like. Removal of organic solvent by in-water-drying is preferred for emulsion based processes. Said processes are well known in this technology area and need not be described further. Air suspension coating provides essentially or exclusively single core microcapsules, whereas the emulsion and spraying based processes tend to provide multicore microcapsules.

The preferred method for application of the release regulating polymer(s) is air suspension coating according to WO 97/14408, incorporated herein by reference, and details in this regard can be obtained from this publication. This method can provide a very rapid evaporation of the organic solvent in which the polymers are dissolved and also allows the use of non-toxic solvents.

The release-controlling polymer can be, without limitation, any polymer that is parenterally administrable and can form a release controlling shell on the cores disclosed in this invention, herein referred to as "shell polymer". It is preferred that the polymer is biodegradable. Specific shell polymers are, for example, polymers or copolymers prepared from alpha-hydroxy acids, preferably lactic acid and/or glycolic acid, or from cyclic dimers selected from glycolides and lactides, for example PLA, PLGA, polytartrate, polyanhydrides, polyorthoesters, polyacetals, poly(ethylene carbonate) copolymers, and copolymers comprising hydroxyl groups and the above-mentioned polymers based on lactic or glycolic acid, for example glucose-PLGA. Mixtures of the polymers can be used. PLGA is preferred. In one embodiment, the release-controlling polymer is not the same polymer that is used to form the core.

The amount and composition of the release regulating polymer that is applied is determined by the desired release characteristics, and depends on several factors, for example the size distribution of the cores, the therapeutic and toxic serum concentrations of the BAS and the desired duration of the release and therapeutic effect. This can be determined by the person skilled in the art by determining the release kinetics in vitro, or preferably in vivo, as a function of the amount of the release regulating shell. It is preferable to obtain an acceptably low burst. Generally, the properties of the release regulating shell is selected so that the release of the BAS starts soon after administration to man to avoid a prolonged lag-phase while still having an acceptably low burst, and to provide a continuous, or essentially continuous, release thereafter. The properties of the shell is also selected so that the release of the BAS is prolonged compared to the release from the cores without said shell, and the duration of release can be for at least 1 day, 3 days, one week, two weeks, about one month or longer. This generally requires about 0.3 to 10, or 0.4 to 6, or 0.5 to 2, or about 0.6 to 1.1 gram of polymer(s) per gram of cores when the core diameter is between 40 to 120 µm.

The release regulating shell (coating) can comprise several different polymers with similar or different chemical composition, in either uncomplexed or complexed form, as well as additives that are applied either in soluble or solid form, for example buffer substances, surface active agents, salts and other ionic compounds. The optimum composition of the shell can be determined by simple experiments, like factorial designs and response surface optimisation, by determining the release kinetics in animal experiments, for example in the rat, pig or monkey. In those cases where antibodies generated against the encapsulated protein affects the evaluation, immunosuppression by methods known in the art can be used or appropriate transgenic animals selected.

Prior to the application of the release-controlling shell, one or several functional substances may be applied onto the cores, referred to herein as "core surface substances". It is preferred that the substances are applied by spraying in an air suspension coating machine. The substance can be dispersed in a solution of the same polymer or a different polymer or a mixture thereof as compared to the one that constitutes the core matrix. Core surface substances useful with the invention can be selected from those that can stabilise pH, improve or control the release kinetics or stability of the BAS. Buffer substances are used in one set of embodiments.

It has been found that it is possible to apply those substances that have a reduced solubility in water, for example zinc oxide, in the form of solid particles without the use of a binder, and this defines one set of embodiments of the invention. The amount of functional substance can be in the range of 0.1-30%, or 0.2-25%, or 0.4 to 20% or even 0.8-15%. The particle size of the functional substance can be below 10 µm, or less than 5 µm, or less than 2 µm, or even less than 1 µm. The substance may be a buffer substance. Examples of "specific particulate buffer substances" of the present invention include magnesium carbonate, magnesium hydroxide, magnesium oxide, magnesium trisilicate, zinc carbonate, zinc hydroxide, zinc oxide, aluminium hydroxide, calcium carbonate, basic aluminium carbonate, ammonium phosphate, calcium phosphate, calcium hydroxide and magaldrate. Zinc carbonate and zinc oxide are preferred. Zinc oxide is used in one set of embodiments.

Generally, air suspension coating provides discrete free flowing microcapsules. Yet, substances can be added onto the surface of the microcapsules to retain the free flowing properties also in those cases where the microcapsules are exposed to a temperature close to or above the glass transition temperature of the polymers in the shell, said substances being referred to herein as "aggregation preventing substances". Said substance can be selected from the following groups: water-soluble saccharides, water-soluble polysaccharides, water-soluble glycosaminoglycans, buffer substances, particulate buffer substances, amino acids, surface active agents, small particles, preferably those which are slightly, very slightly or practically insoluble or insoluble in water, microparticles or nanoparticles comprising biocompatible polymers. Mannitol is used in one set of embodiments. Sodium hyaluronate or sodium carboxymethyl cellulose is used in one set of embodiments.

It has now been found that particles, preferably small particles, can be applied onto the surface of the microcapsule to prevent aggregation, and this is the case in one set of embodiments. Said particles are referred to herein as "aggregation preventing particles" and may be selected to have a limited or very low solubility in water, to dissolve slowly in the body fluids or enzymatically. In one embodiment, particles that dissolve slowly are selected. Examples include the specific particulate buffer substance of the present invention or particles prepared from the specific core polymers of the present invention. Zinc oxide is used in one set of embodiments.

The microcapsules can be stored dry, for example at a temperature in the range of 2 to 25° C., for example via refrigeration. They can be suspended in a suitable liquid prior to administration, for example using a fine needle, with a size 21 G or smaller, preferably 23 G or smaller, and most preferably 25 G or smaller, or as a dry powder. Said administration can be intralipomatous, intramuscular, subcutaneous, or local, for example in a joint, the brain or a specific organ.

Another embodiment of the present invention is directed to the cores and microcapsules obtainable using the processes described above. A core comprises at least one polymer selected from the groups or specific polymers listed above in connection with the process. In one set of embodiments, the core matrix consists of one polymer.

As described for the process, the core matrix may be selected to be one that is not chemically cross-linked. The core can be essentially homogeneous and not hollow. The size of the core is characterised by the diameter, which is determined in the dry state by, for example, light or electron microscopy. For irregularly shaped particles, the longest distance is measured and agglomerates are treated as a single entity. The average diameter is in the range 10-250 µm, or 15-200 µm, or 20-120 µm, or even 30-100 µm. In one embodiment, at least 80% of the cores are in the range 20-180 µm and less than 1% are smaller than 10 µm.

The core contains at least one BAS. It may contain two BASs without any limitation, for example C-peptide and insulin, an interferon and a colony-stimulating factor, for example granulocyte-macrophage stimulating factor and interferon gamma, an antiviral agent and interferon, or one, two or more vaccine components and an adjuvant.

The core releases the BAS within 3 days in one set of embodiments, or within 2 days or even within 1 day, in vivo or under suitable conditions in vitro, and in many cases the cores do not provide sustained release of the BAS. When the desired duration of release is longer than that obtained from the cores, and said cores can be used to manufacture a sustained release formulation with the desired duration, the cores may be defined in this invention as intermediates for producing a sustained release formulation. The in vitro release is determined at 37°. In many cases the cores can simply be dissolved in an aqueous solution or allowed to release the BAS in undissolved state. Enzymes can be used to dissolve the cores when appropriate, especially to simulate the in vivo environment. The cores (30-75 mg) are weighed into a test tube and 1.5 ml of buffer is added and the sample mixed. The buffer is preferably phosphate buffer (30 mM, pH 7.4) with sodium chloride (82 mM) to adjust the ionic strength and optionally appropriate enzymes and agents to obtain the desired enzyme activity enzyme activity, said agents being known in the art, and optional bactericidal agents, for example sodium azide (3 mM). If the integrity of the BAS permits, the samples are placed on a cradle with continuous rocking; otherwise the frequency of rocking is reduced. For amylopectin and maltodextrin cores, α-amylase (185 U/l, final concentration) is added to the buffer. For atelocollagen and gelatin, collagenase and/or matrix metalloproteinase can be added to the buffer. For hyaluronic acid, hyaluronidase can be added. Samples are removed (for example, 1 ml), for example after 1 hour and 0.25, 1, 2 and 3 days, and replaced with the same volume of fresh buffer. The samples are centrifuged (for example at 13 000 rpm for 3 minutes using a Heraeus Biofuge Fresco), the amount of BAS in the supernatant is determined by methods known by the person skilled in the art, for example HPLC analysis, and the fraction of BAS is calculated that has been released from the cores.

The cores can optionally have one or several functional substances applied to their surfaces, in one embodiment not dispersed in a polymer, as described above for the process from which additional details can be obtained. The location of the functional substances between the release controlling shell, which may, for example, generate acid degradation products, and the BAS in the core is a characteristic of the microcapsules of this embodiment and can provide improvements over the prior art, for example avoiding local pH differences and contact between solid buffer particles and sensitive biologically active substances. For example, the BAS and the functional substances may not be in direct contact with each other, or have at most 20%, or at most 10%, or at most 4% or even at most 2% of the BAS at a distance shorter than 0.05 µm, or 0.1 µm, or 0.2 µm, or even shorter than 0.4 µm, from the functional substance.

The microcapsules of the invention comprise a core containing a BAS and a polymer, as well as a release controlling shell, as defined above. The core and the shell can be distinguished from each other by electron microscopy. The polymers in the core and in the shell can have either different or similar properties. Different properties is preferred and most preferably they comprise chemically distinct polymers. The release controlling shell does not contain any BAS in one set of embodiments, for example less than 2% compared to the core, or less than 0.2% or less than 0.01%. In one set of embodiments at least 50%, or at least 80%, or at least 90% or even at least 98% of the microcapsules have one single distinct core.

In one embodiment, the microcapsules of the invention for parenteral administration of a BAS comprise: a) at least one polymer which can be biodegraded with concomitant generation of substances that lower the pH, b) a BAS, and c) at least one solid substance with the ability to stabilise the pH, wherein the BAS is not in contact with, or in proximity of said solid substance. In one set of embodiments, the solid substance c) is essentially localised between the BAS b) and the polymer a). For example, the solid substance c) is not dispersed in a polymer in one set of embodiments.

In another set of embodiments, the microcapsules are further characterised by having an aggregation preventing substance applied to their surfaces, as defined above. In one embodiment, the bioactivity of the BAS is essentially retained, for example at least 70%, or at least 80%, or at least 90% or even at least 97%, as compared to the bioactivity of the BAS before encapsulation. For example, for human growth hormone there is no increase, or an acceptable increase, in the content of dimer or polymer during encapsulation in the core.

In another set of embodiments, the microcapsules contain at least 15% BAS and display an initial release, defined as the area under the concentration-time curve, in the first 24 hours after administration of not more than 20%, preferably not more than 15% and most preferably not more than 10% in excess of the desired release. In another set of embodiments, the microcapsules contain at least 20% BAS and have an initial release of less than 20% for a preparation that provides detectable serum levels of the BAS for one week and less than 10% for a preparation providing detectable serum levels for about two to four weeks. In these embodiments, it is preferable to have a duration of the release of the BAS of at least 1 day, at least 3 days, at least one week, at least two weeks, at least about one month or even longer. These embodiments have been shown to be advantageous when used in combination with protein or peptide BASs, specifically human growth hormone, erythropoietin, interferon gamma and glucagon-like peptides.

EXAMPLES

Example 1

Human growth hormone (GH) was lyophilized in the presence of ammonium acetate (6.3:1 molar ratio ammonium acetate:protein), then suspended in isopropanol and allowed to air dry. Maltodextrin (Paselli MD6, Avebe, Veendam, Holland, 5 g) was dialysed against water (MilliQ, Millipore, 3 times 1500 ml) at 50° C. using a membrane (Spectra/Por) to remove substances with a molecular weight below about 3.5 kDa and then lyophilised. About 18% of low molecular weight glucose-containing material was removed.

Three batches of maltodextrin microspheres were prepared (50% W/W, 1 ml, 1 ml and 1.8 ml, respectively, in sodium acetate, 10 mM, pH 6.4, 2 mM zinc acetate) in which the GH was suspended manually. The compositions were transferred to Miglyol 829 (10, 20 and 30 ml, respectively), W/O emulsions were created by homogenization (Turrax) and left under refrigeration over night (about 16 hours), then centrifuged (Sorvall SS34, 7000 rpm, 10 min) and washed three times with cold acetone (about 30 g, centrifugation 5 min), allowed to air dry and sieved. The batches were sieved and then pooled. The 38-125 µm fraction had a loading of 11% (w/w) and the 125-180 µm fraction 18%, which corresponds to 53% and 90% of the target core load. The protein quality was determined after centrifugation using HPLC size exlusion chromatography (SEC-HPLC, TSK2000 SWxl, Tosoh Corporation) according to Reslow et al. (supra). The dimer content was approximately 3%, compared to about 2.4% in the starting material, and no polymer forms were detected. The fractions were pooled to provide about 0.57 g of cores.

Example 2

GH (20 mg/ml) was precipitated with high efficiency >99%) by addition of zinc acetate (10 mg/ml, 100 µl portions at a time) dissolved in Milli Q water) under magnetic stirring at room temperature to obtain a mole ratio of 3:1 zinc to protein. The stirring was continued over night at room temperature.

Cores were prepared using Zn:GH (700 mg) and sodium hyaluronate (Fermentech, lyophilized and dissolved at 2% in 10 mM sodium acetate+10 mM zinc acetate, pH 5.0 to provide a final concentration of 1% after mixing with GH and additional buffer solution). This composition was divided into 3 batches and for each a W/0 emulsion was created with Miglyol 829 (20 ml) as the external phase (propeller stirring, 810 rpm, 2 min). The discontinuous phase was solidified by pouring into acetone (120 ml) under stirring.

The core loading was about 75% on the pooled batches. Protein integrity was determined after suspending the cores in a buffer (50 mM HEPES, 10 mM EDTA, pH 7.3). After gentle mixing for about one hour the cores had dissolved. No polymers or aggregates of hGH could be detected and the dimer content had increased about 2%.

Example 3

Cores prepared according to Example 1 were coated using air suspension technology essentially according to Example 6 of WO 97/14408, with the addition of magnetic particles to a total of 50 g, using a poly (lactic/glycolic acid) composition of 70% RG502H and 30% RG504H (Boehringer Ingelheim) to a theoretical amount of 0.6 g PLGA/g of cores to prepare a controlled release preparation containing 6.4% (w/w) of GH. Mannitol was applied onto the microcapsules by spraying, which were then dried under vacuum and stored under refrigeration.

Free flowing single core microcapsules were obtained as evaluated by light microscopy. Protein integrity was determined essentially according to Reslow et al. (supra), including removal of the PLGA coating with a mixture of methylene chloride and acetone. No polymer or aggregate forms were detected and compared to the uncoated cores no increase in dimer content was obtained.

Example 4

Cores prepared according to Example 2 were coated and analyzed according to Example 3, with the exception that a theoretical among of 0.8 g PLGA/g of cores was applied. The content of GH in the microcapsules was about 26.3% (w/w), no polymer forms of GH were observed and there was no increase in dimer forms.

Example 5

Figure 1:
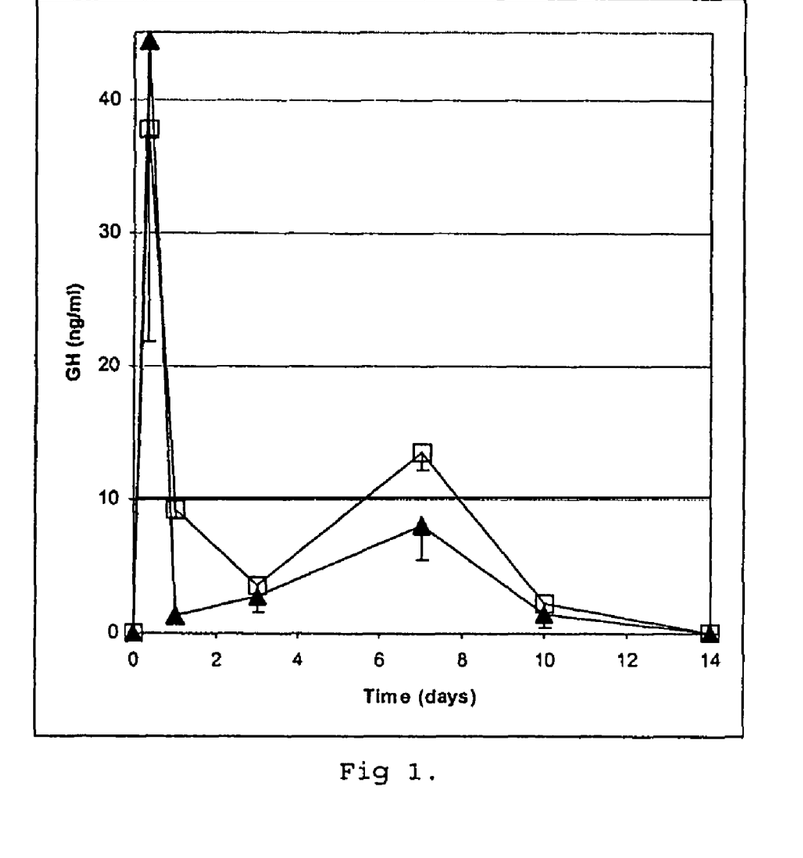
FIG. 1 shows the plasma concentration of hGH hormone as a function of time after subcutaneous administration of the microcapsules prepared in Example 3 (filled triangles) and Example 4 (open squares).
Figure 2:
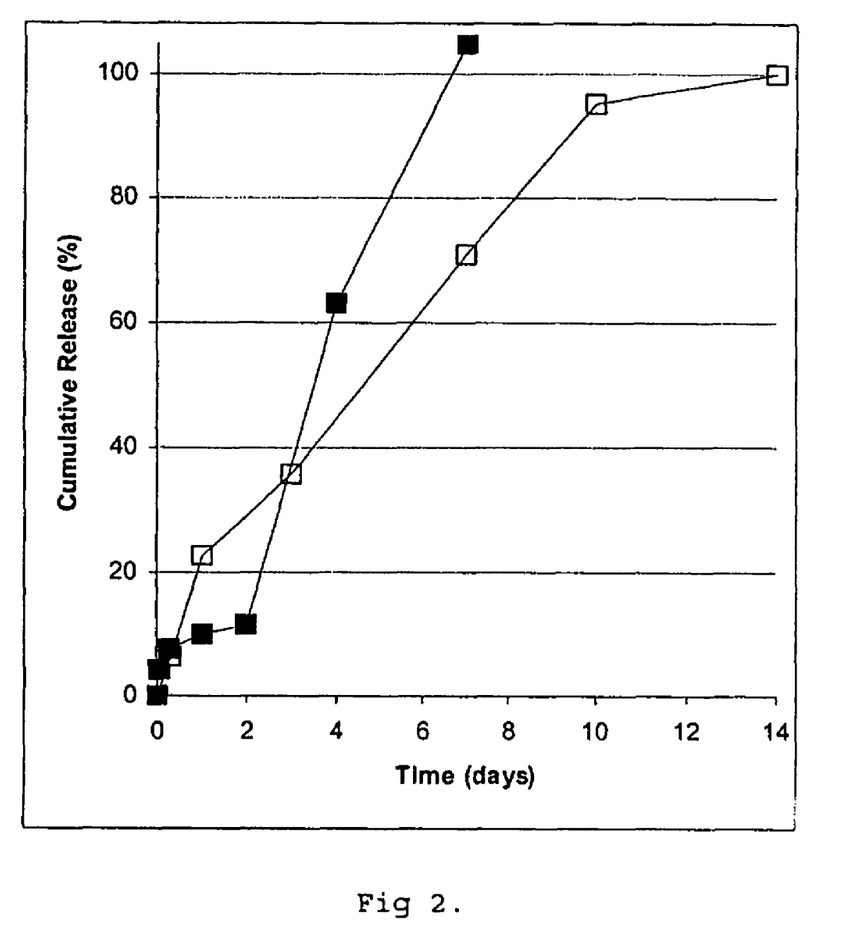
FIG. 2 compares the cumulative release (correlation) of the microcapsules prepared in Example 4 in vitro and in vivo. The in vivo release (open squares) was calculated from the plasma levels assuming 100% bioavailability and the in vitro release (closed squares) was determined according to Reslow et al. (supra) with the exception that only 40 mg of microcapsules were used and no α-amylase was added.

The microcapsules obtained in Examples 3 and 4 were administered subcutaneously in rats (3.5 mg hGH/rat). The preparations were allowed to attain room temperature and then suspended in a solution of sodium carboxymethyl cellulose (Hercules Blanose, type 7LF). The concentration of hGH in plasma was determined (GH IRMA Immunotech IM1397). The results shown in FIG. 1 demonstrate excellent sustained release properties both at a relatively low and a high loading of BAS. The release is continuous and essentially linear, as can be appreciated from the in vitro—in vivo correlation of FIG. 2. The excessive initial release, defined as the observed release during the first 24 hours subtracted with the desired release during the first 24 hours (about 14% for a one week preparation) was about 21% for the microcapsules of Example 3 and about 9% for the microcapsules prepared in Example 4. The latter demonstrates excellent release control at a very high loading. It is clear that the properties of the shell that determines the release properties of the BAS and that the combination of the core, the high content of the BAS in solid form and a shell, the ratio of release regulating polymer to the core, without any BAS encapsulated in the release-regulating polymer, provides unique properties. A preparation providing release of GH for one week can be used to treat conditions requiring parenteral administration of GH. If desired, a further prolongation of the release can be obtained by changing the composition of the coating.

Example 6

GH was lyophilized (250 mg) as described in Example 1, dispersed in isopropanol, allowed to air dry and then mixed with sodium hyaluronate (1%, 550 mg, Fermentech Medical Ltd) dissolved in sodium acetate (10 mM, pH 5.0) containing zinc acetate (10 mM) and PEG (10%, MW 20,000). A water-in-oil emulsion was created with Miglyol 829 (12 g, paddle stirring (2000 rpm, 1 minute). The emulsion was poured into acetone (150 ml). The cores were allowed to sediment and the excess acetone was suctioned off, fresh acetone was added twice and the cores allowed to air dry.

A second batch was also made using this procedure, but the hGH (406 mg) in isopropanol was reduced in size further using a pestle prior to mixing with the sodium hyaluronate solution (about 487 mg) and the amount of acetone was increased acetone (250 ml). The cores were washed twice with acetone (50 ml).

The content of hGH in the cores was about 65% (W/W). The integrity was determined as described above. No polymers or aggregates of hGH could be detected efter immobilisation. The hGH contained approximately 2.4% dimer forms before and 4.4% after immobilisation.

Example 7

Cores were prepared essentially as described for the second batch in Example 6 and microcapsules essentially according to Example 3, with the exceptions that the cores were sieved (<160 µm), the shell polymer was PLGA 65:35 (Lakeshore Biomaterials) and the entire process, including preparation of the cores and application of the coating, was carried out in about 8 hours. No polymer forms of GH were observed, the dimer content increased about 4% during the manufacture of the cores and 2% during the coating. The content of GH was about 24.3% (w/w) in the microcapsules and the in vitro release had a duration exceeding one month.

Example 8

Cores were prepared essentially according to Example 1 or 2 under the conditions summarised in Table 1.

The core polymers (CP) were: CP1: sodium hyaluronate (Fermentech Medical Limited, sterile), CP2: sodium carboxymethyl cellulose (Blanose Type 7LF 00290 Hercules), CP3: gelatin type A (Gelita, 260 bloom), CP4: amylopectin (approx. mw 399 kDa), CP5: amylopectin (approx. 840 kDa), CP6: amylopectin (approx. 3300 kDa, prepared according to Example 2 of WO 02/28909), CP7: maltodextrin (Maltodextrin 6, Avebe), CP8: CP7 dialysed to remove low molecular weight compounds as described in Example 1, CP9: dextran (10%, T2000, Pharmacia), CP10: glycogen (10%), CP11: PEG (10%, 20 kDa), CP12: gelatin type B, Sigma; CP13: amylopectin (approx. 215 kDa), CP14: CP7 cross-flow filtered to remove low molecular weight compounds. The amounts of CP, BAS, DP and CO are expression in either of weight (g), concentration (%) or volume (ml).

The BASs were: BAS1: hGH lyophilised in the presence of ammonium acetate according to Example 1, BAS2: hGH precipitated with zinc according to Example 2, BAS3: hGH precipitated using polyethylene glycol according to Reslow et al. (supra), BAS0: porcine somatotropin precipitated with zinc acetate (mole ratio 3:1 Zn:protein) in sodium bicarbonate buffer at pH about 9.2, BAS5: zinc insulin (Ultratard, Novo Nordisk); BAS6: naltrexone base, BAS7: loperamide base, BAS8: triptorelin pamoate, BAS9: C-peptide (precipitated at about pH 3.5, lyophilised and reduced in size with a pestle), BAS10: starch granules (Cerestar 06090, model for undissolved BASs); BAS11: bovine serum albumin (BSA), model for dissolved BASs, BAS12: porcine somatotropin lyophilized in the presence of ammonium acetate (2 mg/ml, 10:1 ammonium acetate:protein), BAS13: loperamide hydrochloride.

The continuous phases (CO) were: C01: Miglyol 829, CO2: polyethylene glycol (40% average molecular weight 20 kDa) dissolved in an aqueous solution, CO3: rapeseed oil, CO4: PEG (20% 6 kDa), CO5: cold gas (gaseous+liquid nitrogen).

The solidification principles (SP) were: SP1: exposure to acetone; SP2: physical crosslinking; SP3: complex formation with benzalkonium chloride (1 mg/ml) in the acetone used for solidification; SP4: exposure to ethyl acetate; SP5: freezing in an emulsion by placing the vessel in another vessel containing acetone and dry ice, SP6: exposure to isopropanol, SP7: freezing in cold gas.

The work up (WU) procedures were: WU1: removal of oil by filtration using a 0.45 µm filter in a centrifuge tube (Millipore, PVDF) and washing three times with acetone (5° C.) and air drying; WU2: washing with acetone three times and air drying; WU3: washing with ethyl acetate and air drying, WU4: extraction of PEG with cold (4° C.) acetone and air drying, WU5: washing with 10 mM sodium acetate, 10 mm zinc acetate, pH 7.3, WU6: isopropanol, WU7: evaporation of liquid nitrogen and lyophilization.

Diluent particles (DP) were: DP1: starch granules, DP2: sucrose particles formed from a solution during core preparation, DP3: PLGA microspheres (RG502H).

The BAS/core polymer ratio (BCR) was calculated as the dry weight of the BAS divided by the combined dry weight of the BAS and the polymer is expressed in weight percent in the BCR column and the obtained loading in the LO column. The presence of cores with a size acceptable for air suspension coating, optionally after sieving, was evaluated by light microscopy (column LM). The time for solidification is given as 0.1 hour when not exceeding 6 min. The core loadings were generally determined by HPLC, but in experiments 14-16, 18 and 40, spectrophotometry was used to obtain approximate values.

The reference example R1 shows that cores of hyaluronic acid could not be prepared in the absence of an undissolved BAS.

The reference examples R2 and R3, as compared to the Experimental examples #1 and #2, show that this maltodextrin cannot be used at high concentration and solidification by physical cross-linking for the manufacture of cores without prior removal of low molecular weight compounds. The experiments 11-13 demonstrate how the content of BAS in the cores can be controlled by addition of diluent particles. In Experiment 20 CP1+BAS11+DP2, were all dissolved in the same solution to concentrations of 2%, 0.7% and 60%, respectively, and the sucrose diluent particles were formed during the core preparation. In Experiment 24-26 the same approach was used, but the BAS omitted and the concentration of CP1 varied; in this case the addition of benzalkonium chloride improved the solidification to yield more discrete cores. Experiment 27 was the same, apart from the concentration of sucrose (50%), CP1 (1%) and BAS11 (0.7%).

Example 9

Cores were prepared by spraying a composition (5 g) comprising sodium hyaluronate (67% w/w, 1% aqueous solution, Fermentech) and starch granules, as a model for an undissolved BAS (33% w/w), giving a BAS/core polymer ration of about 98%, and freezing using a cold gas. The composition was fed into a pneumatic spray nozzle normally used in an air suspension coater (Hüttlin Kugelcoater, 1 mm nozzle diameter) during about one minute using a syringe and sprayed into a stainless steel vessel, which contained liquid nitrogen and a magnetic stirrer. The nozzle was fed with spraying air (1.5 bar) and microclimate air (0.5 bar) from the Kugelcoater. The frozen droplets were transferred to a steel tray and placed in a freeze dryer immediately after the nitrogen had evaporated. Cores suitable for air suspension coating were obtained after sieving.

Example 10

Procedure for Manufacturing Cores Comprising a Water Insoluble Core Polymer

Cores comprising a BAS were prepared by suspending loperamide hydrochloride (300 mg) in a solution of PLGA (150 mg Resomer RG756, ethyl acetate to 2.86 g), creating an emulsion with an external aqueous phase (13.1 g) comprising PVA (0.5%, 86-89% hydrolyzed, 15 kDa), sodium carboxymethylcellulose (1.5%, Blanose 7LF) and citrate/phosphate buffer (2.5 mM, pH 7.6). The organic phase was extracted with additional citrate/phosphate buffer (5 mM, pH 7.6, 200 g) for about one hour, the cores were washed on a filter using the same buffer followed by water (MilliQ) prior to lyophilization. The cores were sieved (<160 µm) and the content of BAS determined to about 61% by HPLC.

Example 11

Injectability of Microcapsules

Microcapsules were prepared essentially according to Example 2 and 4, the BAS being porcine somatotropin lyophilized in the presence of ammonium acetate, sieved dry (50-100 µm) and reconstituted with sodium carboxymethyl cellulose (Hercules Blanose, type 7LF, 3.5%, autoclaved,) to a concentration of 10% by weight. The microcapsules were easily injected into pig meat with rind using a 25 G needle (Terumo).

TABLE 1

Core preparations.

| # | CP | CP (g) | CP % | BAS | BAS (g) | BCR (%) | DP | DP (g) | CO | CO (ml) | CO (%) | SP | T (h) | WU | LM | LO (%) |
|---|----|--------|------|-----|---------|---------|-----|--------|-----|---------|--------|-----|-------|-----|-----|--------|
| R1 | 1 | 0.1 | 1 | — | — | — | — | — | 1 | 6 | — | 1 | 0.1 | 2 | No | — |
| R2 | 7 | 1 | 50 | — | — | — | — | — | 3 | 10 | — | 2 | 1 | 2 | No | — |
| R3 | 7 | 1 | 50 | — | — | — | — | — | 2 | 10 | 30 | 2 | 1 | 2 | No | — |
| 1 | 8 | 1 | 50 | — | — | — | — | — | 3 | 10 | | 2 | 0.3 | 2 | Yes | — |

TABLE 1-continued

Core preparations.

| # | CP | CP (g) | CP % | BAS | BAS (g) | BCR (%) | DP | DP (g) | CO | CO (ml) | CO (%) | SP | T (h) | WU | LM | LO (%) |
|---|----|--------|------|-----|---------|---------|-----|--------|-----|---------|--------|-----|-------|-----|-----|--------|
| 2 | 8 | 1 | 50 | — | — | — | — | — | 2 | 10 | 30 | 2 | 1 | 2 | Yes | — |
| 3 | 1 | 3.33 | 1 | 13 | 1.67 | 98 | — | — | 5 | — | — | — | 0.1 | 7 | Yes | 81 |
| 4 | 2 | 0.4 | 10 | 10 | 0.2 | 83 | — | — | 1 | 6 | — | 1 | 0.1 | 2 | Yes | — |
| 5 | 4 | 0.4 | 10 | 10 | 0.2 | 83 | — | — | 1 | 6 | — | 1 | 0.1 | 2 | Yes | — |
| 6 | 5 | 0.4 | 10 | 10 | 0.2 | 83 | — | — | 1 | 6 | — | 1 | 0.1 | 2 | Yes | — |
| 7 | 8 | 0.4 | 10 | 10 | 0.2 | 83 | — | — | 1 | 6 | — | 1 | 0.1 | 2 | Yes | — |
| 8 | 9 | 0.4 | 10 | 10 | 0.2 | 83 | — | — | 1 | 6 | — | 1 | 0.1 | 2 | Yes | — |
| 9 | 10 | 0.4 | 10 | 10 | 0.2 | 83 | — | — | 1 | 6 | — | 1 | 0.1 | 2 | Yes | — |
| 10 | 11 | 0.4 | 10 | 10 | 0.2 | 91 | — | — | 1 | 6 | — | 1 | 0.1 | 2 | Yes | — |
| 11 | 1 | 0.2 | 1 | 4 | 0.1 | 98 | — | — | 1 | 20 | — | 1 | 0.1 | 2 | Yes | 83 |
| 12 | 1 | 0.2 | 1 | 4 | 0.05 | 96 | 1 | 0.05 | 1 | 20 | — | 1 | 0.1 | 2 | Yes | 49 |
| 13 | 1 | 0.2 | 1 | 4 | 0.01 | 91 | 1 | 0.09 | 1 | 20 | — | 1 | 0.1 | 2 | Yes | 15 |
| 14 | 1 | 0.2 | 1 | 8 | 0.1 | 99 | — | — | 1 | 20 | — | 4 | 0.1 | 3 | Yes | 100 |
| 15 | 1 | 0.2 | 1 | 7 | 0.1 | 99 | — | — | 1 | 20 | — | 4 | 0.1 | 3 | Yes | 91 |
| 16 | 1 | 0.2 | 4 | 6 | 0.05 | 93 | — | — | 1 | 20 | — | 4 | 0.1 | 3 | Yes | 12 |
| 17 | 1 | 0.2 | 1 | 5 | 0.1 | 99 | — | — | 1 | 20 | — | 4 | 0.1 | 3 | Yes | — |
| 18 | 1 | 0.1 | 1 | 9 | 0.05 | 98 | — | — | 1 | 20 | — | 4 | 0.1 | 3 | Yes | 80 |
| 19 | 1 | 0.2 | 1 | 10 | 0.1 | 98 | — | — | 1 | 20 | — | 5 | 0.5 | 4 | Yes | — |
| 20 | 1 | — | — | 11 | — | 26 | 2 | — | 1 | 10 | — | 5 | 0.5 | 4 | Yes | — |
| 21 | 13 | 0.2 | 40 | 10 | 0.1 | 56 | — | — | 1 | 5 | — | 5 | 1 | 4 | Yes | — |
| 22 | 6 | 0.2 | 10 | 10 | 0.1 | 83 | — | — | 1 | 20 | — | 1 | 0.1 | 2 | Yes | — |
| 23 | 3 | 6.9 | 25 | 3 | 0.4 | 23 | — | — | 3 | 72 | — | 2 | 16 | 1 | Yes | 16 |
| 24 | 1 | — | 2.9 | — | — | — | 2 | — | 1 | 20 | — | 1 | 0.1 | 2 | Yes | — |
| 25 | 1 | — | 3.6 | — | — | — | 2 | — | 1 | 20 | — | 1 | 0.1 | 2 | Yes | — |
| 26 | 1 | — | 2.9 | — | — | — | 2 | — | 1 | 20 | — | 3 | 0.1 | 2 | Yes | — |
| 27 | 1 | — | 1 | 11 | — | 41 | 2 | — | 1 | 20 | — | 3 | 0.1 | 2 | Yes | — |
| 28 | 13 | 0.15 | 30 | 12 | 0.05 | 53 | — | — | 4 | 5 | — | 5 | 0.25 | 4 | Yes | — |
| 30 | 13 | 0.1 | 29.5 | 12 | 0.05 | 63 | — | — | 4 | 5 | — | 2 | 2 | 5 | Yes | — |
| 31 | 13 | 0.1 | 34.5 | 12 | 0.05 | 59 | — | — | 1 | 5 | — | 2 | 1 | 5 | Yes | — |
| 32 | 14 | 0.06 | 30 | 12 | 0.03 | 63 | — | — | 4 | 5 | — | 2 | 2 | 5 | Yes | — |
| 33 | 14 | 0.06 | 30 | 12 | 0.03 | 63 | — | — | 1 | 5 | — | 2 | 2 | 5 | Yes | — |
| 34 | 13 | 0.2 | 40 | 10 | 0.1 | 56 | — | — | 4 | 5 | — | 5 | 0.5 | 4 | Yes | — |
| 35 | 1 | 0.2 | 1 | 10 | 0.1 | 98 | — | — | 1 | 20 | — | 6 | 0.1 | 6 | Yes | — |
| 36 | 12 | 2.4 | 25 | 3 | 0.17 | 12 | — | — | 3 | 24 | — | 2 | 16 | 1 | Yes | 18 |
| 37 | 1 | 0.25 | 1 | 1 | 0.08 | 91 | — | — | 1 | 20 | — | 1 | 0.1 | 2 | Yes | 78 |
| 38 | 1 | 0.48 | 1 | 2 | 0.23 | 83 | — | — | 1 | 20 | — | 1 | 0.1 | 2 | Yes | 75 |
| 39 | 1 | 0.4 | 1 | 12 | 0.1 | 96 | 3 | 0.05 | 1 | 20 | — | 6 | 0.1 | 6 | Yes | 29 |
| 40 | 1 | 3.3 | 1 | 13 | 1.67 | 98 | — | — | 5 | — | — | 7 | 0.1 | 7 | Yes | 81 |

The invention claimed is:

1. A process for producing parenterally acceptable cores which comprises the following steps:
   a) preparing an aqueous polymer solution of at least one polymer, said polymers being acceptable for parenteral administration and selected from protamin, polyarginine, polyomithine, sodium carboxymethylcellulose, maltodextrin, dextran, glycogen, hyaluronic acid, chondroitin sulphate, dermatan sulfate, polyvinylpyrrolidone, polyethyleneglycol and polyethyleneoxide, wherein the polymer concentration is in the range 0.5-15%, with the proviso that when the dispersing in step d) is carried out by atomization said polymer concentration is less than 5%,
   b) providing at least one parenterally administrable biologically active substance in undissolved form,
   c) combining the polymer solution of step a) with the biologically active substance of step b), in a ratio to said polymer such that when expressed by weight percentage the biologically active substance constitutes at least 30 percent of the dry weight of the combined weight of said polymer and said biologically active substance,
   d) dispersing the composition obtained in step c) as a discontinuous phase in a continuous phase,
   e) solidifying the composition, to provide cores suitable for air suspension coating, wherein the obtained cores have a size distribution such that at least 80% of the obtained cores measure from 10-200 μm.

2. The process according to claim 1, wherein the obtained cores are suitable for air suspension coating after drying.

3. The process according to claim 1, comprising applying one or several core surface substances onto the cores, by spraying in an air suspension coating machine, said substances preferably being selected from those that can stabilise pH, reduce aggregation, improve stability or influence the release kinetics of the biologically active substance.

4. The process according to claim 1, wherein said ratio in step c) is at least 40%.

5. The process according to claim 1, wherein said ratio in step c) is at least 50%.

6. The process according to claim 1, wherein said ratio in step c) is at least 70%.

7. The process according to claim 1, wherein the solidification of step e) is carried out by a solidification process selected from the group consisting of exposure of the discontinuous phase to one or more organic solvents, formation of physical cross-links, formation of a complex, freezing, freeze drying and combinations thereof.

8. The process according to claim 7, wherein the continuous phase is selected from the group consisting of: one or more organic solvents, one or more oils, an aqueous solution containing one or more polymers, a gas and combinations thereof.

9. The process according to claim 1, where the biologically active substance in step b) is a protein or peptide.

10. The process according to claim 1, comprising the step of applying a release-controlling shell onto a core obtained in step e).

11. A process for producing parenterally acceptable cores which comprises the following steps:
- a) preparing an aqueous polymer solution of at least one polymer, said polymers being acceptable for parenteral administration and selected from hyaluronic acid, chondroitin sulphate, dermatan sulfate, in a concentration lower than 5% based on dry weight,
- b) providing at least one parenterally administrable biologically active substance in undissolved form,
- c) combining the polymer solution of step a) with the biologically active substance of step b), in a ratio to said polymer such that when expressed by weight percentage the biologically active substance constitutes 30-99 percent of the dry weight of the combined weight of said polymer and said biologically active substance,
- d) dispersing the composition obtained in step c) as a discontinuous phase in a continuous phase, and
- e) solidifying the composition to provide cores suitable for air suspension coating, wherein the obtained cores have a size distribution such that at least 80% of the obtained cores measure from 10-200 μm.

12. The process according to claim 11, wherein the concentration of aqueous polymer solution in step a) is lower than 4 percent based on dry weight.

13. The process according to claim 11, wherein the concentration of aqueous polymer solution in step a) is lower than 3 percent based on dry weight.

14. The process according to claim 11, wherein said ratio in step c) is at least 40-99 percent.

15. The process according to claim 11, wherein said ratio in step c) is at least 70-99 percent.

16. The process according to claim 11, wherein the solidification in step e) is by rapid-freezing.

17. The process according to claim 16, wherein a liquefied gas is used to obtain freezing.

18. The process according to claim 11, comprising the step of applying a release-controlling shell onto a core obtained in step e).

19. The process according to claim 18, wherein said application is carried out by air suspension coating.

20. A process for preparing a parenteral sustained release microcapsule which comprises the following steps:
- a) preparing an aqueous polymer solution of a parenterally administrable polymer and selected from hyaluronic acid or chondroitin sulphate, wherein the concentration of said polymer is lower than 5%, preferably less than 4%,
- b) providing at least one parenterally administrable biologically active substance in undissolved form,
- c) combining the polymer solution of step a) with the biologically active substance of step b), in a ratio to said polymer such that when expressed by weight percentage the biologically active substance constitutes 30-99 percent of the dry weight of the combined weight of said polymer and said biologically active substance,
- d) dispersing the composition obtained in step c) as a discontinuous phase in a continuous phase, wherein said continuous phase is a gas,
- e) solidifying the composition of step d) by freezing using a liquefied gas to provide cores having a diameter between 40 and 120 μm and being suitable for air suspension coating, and,
- f) applying a release controlling shell onto said cores, wherein the release controlling polymer is about 0.3 to 10 gram of polymer(s) per gram of cores.

* * * * *